United States Patent [19]

Eby, III

[11] Patent Number: 4,956,385

[45] Date of Patent: Sep. 11, 1990

[54] METHOD FOR REDUCING THE DURATION OF THE COMMON COLD

[76] Inventor: George A. Eby, III, 2109 Paramount St., Austin, Tex. 78704

[21] Appl. No.: 102,750

[22] Filed: Sep. 24, 1987

Related U.S. Application Data

[63] Continuation of Ser. No. 667,097, Nov. 1, 1984, abandoned, which is a continuation-in-part of Ser. No. 378,479, May 14, 1982, Pat. No. 4,503,070, which is a continuation-in-part of Ser. No. 288,750, Jul. 31, 1981, abandoned.

[51] Int. Cl.$^5$ .......................... A61K 9/10; A61K 9/68; A61K 31/315; A61K 33/30
[52] U.S. Cl. ...................................... 514/494; 424/46; 424/48; 424/439; 424/440; 424/441; 424/442; 424/464; 424/489; 424/641; 424/643; 514/888
[58] Field of Search ................. 514/494, 888; 424/289, 424/145, 46, 48, 439, 440, 441, 442, 464, 489, 641, 643

[56] References Cited

U.S. PATENT DOCUMENTS

| | | | |
|---|---|---|---|
| 944,738 | 12/1909 | Loose et al. | 474/95 |
| 4,367,218 | 1/1983 | Jacobson | 424/49 |
| 4,444,755 | 4/1984 | Horrobin | 424/145 |
| 4,469,674 | 9/1984 | Shah, et al. | 474/52 |

OTHER PUBLICATIONS

*Handbook of Nonprescription Drugs*, 6th ed., American Pharmaceutical Association, p. 317.
*The Pharmacological Pharmacological Basis of Therapeutics*, 5th ed., ed. by Goodman and Gilman, Macmillan Publishing Co., Inc., 1975, pp. 1000–1001.
Gutman, *Modern Drug Encyclopedia and Therapeutic Guide*, New Modern Drugs, N.Y., p. 731.
Bailey, *British Medical Journal*, Apr. 17, 1973, p. 808.
Merck's 1901 Manual, Merck and Co., N.Y., pp. 124–126.
*Merck's Manual of the Materia, Medica*, 5th ed., Merck and Co., N.Y., 1923, pp. 160–161.
Howard, *Modern Drug Encyclopedia*, 6th ed., Drug Publications, Inc., N.Y., p. 1168.
Korant, *Nature*, 248, 1974, pp. 588–590.
Korant, *Chem. Abst., vol. 85, p. 76, 1976, Abst. No. 814y*.
Franklin, *Brit. Med. Journal*, pp. 1115–1116, 1931.
Shields, *The Practitioner*, pp. 645–648, 1936 (copy attached).
Eby, et al. (Jan. 1984), *Antimicrobial Agents and Chemo.*, 25:20–24.
The Merck Index, 10th edition, 1983, pp. 1455–1458.
Eby (Nov. 1980), "Zinc in Leukemia . . . ".
Korant (1979), "Role of Cellular and Viral Proteases".
Korant, et al. (1976), *Jrnl. Virol.*, 18:298–306.
Butterworth, et al. (1976), *Arch Virol.*, 51:169–189.
Korant, et al. (1973), "Zinc Ions Inhibit Replication of Rhinoviruses".
Marone, et al. (1980), Jrn. All. Clin. Immunol., 65:171.
Howard, Modern Drug Encyclopedia.
Gutman (1941), *Modern Drug Encyclopedia*.
Shields (1936), "The Ionization Treatment of Hay Fever", pp. 645–648.
Godfrey (1988), *Antimicrob. Agents Chemother.,*32:605.
Farr et al. (1988). *Antimicrob Agents Chemothr.*, 32:607.
Martin (1988), *Antimicrob. Agents Chemother.*, 32:600.
Farr et al. (1987), *Antimicrob. Agents Chemother.*, 31:1183.
Al–Nakib et al. (1987), *Jrnl. Antimicrob. Chemother.*, 20:893.
Pasternak (1987), *Bioscience Rep.*, 7(02):81.
"Zinc Zaps Common Cold" (1987), *The Evening Wellington*, New Zealand.
Zerial et al. (1985), *Antimicrob. Agents Chemother.*, 27(5):846.
"Zinc vs Colds" (1984), Austin American Statesman, Dec. 2, 1984, p. A15.
Eby et al. (1988), *Antimicrob. Agents Chemother.*, 32:606.
Couch (1984), *Jrnl. Infect. Dis.*, 150(2):174.
Hayden et al. (1984) *Jrnl. Infect. Dis.*, 150(2):174.
Samo et al. (1984), *Jrnl. Infect. Dis.*, 150(2):181.
Phillpotts et al. (1983) *Antimicrob. Agents Chemother.*, 23(5):671.
Anderson et al. (1983), "Viral Respiratory Illnesses", *Medical Clinics of North America*, 67(5):1009.
Levandowski et al. (1982), *Antimicrob. Agents Chemother.*, 22(6):1004.
Andermann et al. (1982), *Eur. Jrnl. Drug Metab. Pharma.*, 7(8):233.
Hayden et al. (1982), *Antimicrob. Agents Chemother.*, 21(6):892.
"Idoxuridine and Some Other Antiviral Agents" (1982), *Martindale, The Extra Pharmacopoeia*, 28th Edition, pp. 820–827.
Giron (1982), *Proc. Soc. Exp. Biol. Med.*, 170.25.
Korant (1979) "Inhibition of Viral Protein Cleavage", in *Design of Inhibitor of Viral Functions*, I. Gauri, ed., Academic Press.
Korant (1979), "Role of Cellular and Viral Proteases . . ." in *The Molecular Biology of Picornoviruses*, pp. 149–173.
Webster's New Collegiate Dictionary (1979), "lozenge and troche".
Butterworth et al. (1976), *Arch. Virol.*, 51:109.

(List continue on next page.)

*Primary Examiner*—Ronald W. Griffin
*Attorney, Agent, or Firm*—Arnold, White & Durkee

[57] ABSTRACT

This invention discloses and claims improved methods to reduce duration of common colds in humans through use of pharmaceutically acceptable zinc compounds topically and frequently applied to the oral mucosa by various means. The invention improves upon the prior art using zinc gluconate throat lozenges to reduce the duration of common colds and zinc borate intranasally as an astringent and decongestant in treatment of common colds.

32 Claims, No Drawings

OTHER PUBLICATIONS

Harmon et al. (1976), *Proc. Soc. Exp. Biol. Med.*, 152:598.

1948 Quarterly Cumulative Index Medicus, vol. 44, p. 797.

Van Voris, "Antiviral Chemotherapy", Chapter 8 in *Textbook of Human Virology*, pp. 193–229.

Levandowski, "Rhinoviruses", Chapter 16 in *Textbook of Human Virology, pp. 391–405.*

Tyrrell et al., "Antirhinovirus Drugs", pp. 340–341.

Chapter 57, "Antiviral Chemotherapy & Prophylaxis," in Review of Medical Pharmacology, 7th Edition, Meyers et al. eds., pp. 589–592.

Akzo Chemie "Gluconates", pp. 5–15.

METHOD FOR REDUCING THE DURATION OF THE COMMON COLD

This application is a continuation of application Ser. No. 667,097, filed Nov. 1, 1984, which is a continuation-in-part of "A Method for reducing the duration of the common cold" U.S. Pat. No. 4,503,070 issued Mar. 5, 1985 on Ser. No. 378,479 filed May 14, 1982 which is a continuation-in-part of "A Rapid Acting Treatment for the Common Cold" Ser. No. 288,750 filed July 31, 1981, now abandoned, which is a continuation-in-part of Ser. No. 222,620, filed Jan. 5, 1981, now abandoned.

FIELD OF INVENTION

This invention relates to improved methods for reducing the duration of common colds in humans.

BACKGROUND

The art of managing viral upper respiratory infections commonly called common colds was not adequate prior to my discovery that frequently administered zinc gluconate lozenges reduce the duration of common colds. Common colds are the most common acute illness in the United States and account for about one-half of all lost school days and lost work days. An estimated one billion colds occur in the United States each year. Thus, there can be no question as to the need for safe, simple, inexpensive, effective and available treatments to minimize or eliminate this important and costly public health problem.

Before my discovery of the effectiveness of zinc gluconate lozenges in reducing the duration of the common cold (see U.S. Pat. No. 4,503,070), treatment of common colds involved use of symptomatic therapy. Such therapy did not reduce duration of common colds. For example, with or without treatment, duration of 50% of the common colds caused by rhinoviruses remained at 7 days. Primary common colds symptoms are nasal drainage and nasal congestion. Secondary symptoms often accompanying primary symptoms include: headache, fever, myalgia, sneezing, sore throat, scratchy throat, cough and hoarseness. The prior art teaches individual treatment of each symptom as needed to ameliorate symptoms during their association with a common cold, rather than teaches treatment of the common cold to reduce the duration of all symptoms associated with them.

PRIOR ART

It has been established in vitro that zinc ions can inhibit replication of a few of the many antigenically different rhinoviruses. The concentration of zinc ions required to be antirhinoviral has been reported to be 0.1 mM or greater which is 10 times or greater than the zinc ionic concentration found in human serum. But other in vitro studies have demonstrated that inhibitory effects of zinc on rhinoviruses are reversible and provide no lasting effect once the zinc ions are removed from the medium. According to the latter studies, when zinc is removed from rhinoviruses, they resume their replication and again become fully infective. The best use for zinc in activities involving the rhinoviruses was suggested to be as a method to temporarily or reversibly inhibit rhinovirus replication in laboratory experiments. Since the antirhinoviral effect was observed to be reversible and since the inhibitory effects had been demonstrated in only a few of the antigenically different viruses known to cause the common cold, zinc was not considered to be a suitable antirhinoviral agent for the treatment of the common cold in humans. It was unknown as to how zinc could be kept in the superficial columnar cells of the nose in which the viruses are believed to be replicating for a sufficiently long period of time to stop viral replication as intranasally administered substances are rapidly cleared from the nose. Additionally, it has been found that administration of zinc gluconate lozenges does not cause an increase in the zinc content of nasal mucous.

It has been established that zinc can provide an astringent and decongestant effect in common cold treatment. Zinc inhibits the release of histamine from mast cells and basophils. Histamine is a mediator of two primary common cold symptoms (nasal drainage and nasal congestion). The effect of zinc in inhibiting the release of histamine from mast cells and basophils produces a reduction in histamine mediated nasal drainage and nasal congestion, which might be considered as astringent-like and decongestant. A technique used earlier in this century to provide astringent and decongestant effects in the treatment of common colds requires that 4 to 10 drops of a 0.2% to 2.0% zinc borate aqueous suspension be applied by spray, instillation or Dowling packing into each nostril or eye several times per day. Such an intranasal method operates only to relieve the treated human from certain discomfort associated with the congestion symptoms. I have previously disclosed that the low dosages of zinc and the method of application only brings temporary relief, perhaps because natural circulation removes zinc ions from the locus of the treatment more rapidly than the low application rate of zinc ions by the dosages replaces them. Because it has been established in vitro that zinc ions can inhibit replication of rhinoviruses, one may theorize that a low dosage of zinc may produce a zinc ion concentration that may or may not reach antiviral concentrations and that a method of application that does not maintain a sufficiently high level of zinc ions in the locus of treatment would not prevent continued viral replication. Regardless of a theoretical justification for a method of increasing zinc ion concentration, the astringent-like and decongestant effects of the low zinc dosages under the prior art methods of application cease when the treatment is discontinued before the cold has run its normal, untreated duration.

My discovery that zinc gluconate lozenges dissolved in the mouth at frequent intervals reduced the duration of common colds by about 7 days (Antimicrobial Agents and Chemotherapy, Vol. 25, No. 1, Pages 20 to 24) led to a search for improved methods of using zinc to reduce the duration of common colds. For unknown reasons, not all compounds of zinc, dosage, frequencies of administration or means of zinc administration are effective in reducing the duration of common colds. For example, zinc orotate lozenges containing 37 mg zinc used each 3 hours failed to produce any difference in duration of common colds as compared to placebo. Similarly 10 mM zinc gluconate nasal spray, used several times daily up to once each 15 minutes, failed to produce any difference in duration of common colds as compared to placebo.

OBJECTIVE OF INVENTION

Accordingly, the objective of this invention is to correct deficiencies of the prior art in treatment of common colds through improvements in the administration of zinc that significantly reduce duration of common colds in humans.

SUMMARY OF INVENTION

This invention relates to improved treatments that shorten duration of common colds through use of zinc compounds applied in a manner and at a frequency so as to cause a sustained, above normal concentration of zinc ions in the virally infected tissues until no common cold symptoms remain and without relapse of any common cold symptom.

DETAILED DESCRIPTION OF INVENTION

The invention disclosed and claimed are methods to reduce duration of common colds in humans as evinced by reduction of duration of 10 common cold symptoms defined as being: nasal drainage, nasal obstruction, headache, fever, myalgia, sneezing, sore throat, scratchy throat, cough and hoarseness with each symptom, when present, being a result of a viral upper respiratory infection. Such methods involve improvements in the administration of pharmaceutically acceptable zinc compounds topically applied to oral, pharyngeal and/or nasal mucosal membranes using means that raise the concentration of zinc ions in virally infected areas. Those concentrations are maintained for a period of time until all common cold symptoms are eliminated without relapse.

Means of application include, but are not limited to the following direct, indirect, carrier, and special means or any combination of means. Direct application of zinc compounds may be by nasal sprays, nasal drops, nasal ointments, nasal washes, nasal injections, nasal packings, or indirectly through use of throat lozenges, or through use of mouthwashes or gargles, or through the use of ointments applied to the nasal nares, the bridge of the nose, or the face or any combination of these and similar methods of application. Carriers such as dimethyl sulfoxide and other special methods such as oral ingestion or parenteral introduction of zinc compounds where such treatment allows elevation of zinc ionic concentration in virally infected areas may be used as needed and given by any means of administration. The forms in which the zinc compounds may be administered include but are not limited to lozenges, troches, candies, injectants, chewing gums, tablets, powders, sprays, liquids, ointments, and aerosols. Pharmaceutically acceptable zinc compounds in dosages up to 500 milligrams of zinc include but are not limited to zinc gluconate, zinc ascorbate, zinc citrate, zinc oxide, zinc acetate, zinc picolinate, zinc transferrin, and zinc aspartate. Additional forms of zinc that offer improved taste performance include zinc glycinate and the D, L and DL forms of zinc alaninate, zinc lysinate, zinc leucinate, zinc alpha-aminobutyrate, zinc valinate, zinc iso-leucinate and zinc iso-valinate. Other forms that offer improved performance are fat soluble forms such as zinc sterate and zinc oleate and a mast cell biochemically natural form, zinc-heparin complex.

OPERATIONAL METHODS TO DEMONSTRATE IMPROVED INVENTION

Humans in need of improved treatment may treat their oral mucosa, or have their oral mucosa treated so as to saturate the lining of the mouth, throat and tongue with zinc ions with up to 500 milligrams of zinc, in any improved pharmaceutically acceptable form, at treatment intervals varying from minutes to hours until the human undergoing treatment is asymptomatic. Doses are preferred to each contain less than 50 mg of zinc applied preferably each 1 to 4 hours although larger doses may be applied but at longer, more convenient, treatment intervals. Smaller doses may be swallowed while larger doses may be expectorated. Larger doses, expectorated to prevent excessive ingestion of zinc, may provide more rapid results compared to the original invention. Each dose is kept in contact with the oral mucosa as long as necessary in order to improve performance over the original invention. Improved means of administration of zinc to the oral mucosa may be by any means such as gargles, mouth rinses, lozenges, troaches, chewing gums, candies, powders and sprays so long as it offers improved performance over the original invention by way of convenience, palatability, safety or further reduction in the duration of common colds. Zinc concentration in saliva by such treatment must be in excess of 0.1 mM and should not be more than 1 molar and preferably in the 1 to 300 mM range although 5 mM to 50 mM may be even more preferable. Treatment should be started as early as possible to maximally reduce the duration of common colds. There are no known contraindications to the treatment so long as the dosage does not exceed that amount which produces vomitting or other systemic side effects and treatment is not used for more than 14 days.

What is claimed is:

1. A method for treating the common cold comprising:
   (a) applying an effective dosage of a pharmaceutically acceptable saliva soluble and ionizable zinc compound other than zinc gluconate to the oral mucosa of a human in need of treatment;
   (b) permitting said zinc compound to remain in contact with the oral mucosa for a period of time necessary for the zinc thereof to saturate the oral mucosa; and
   (c) applying additional dosages of such a zinc compound in like fashion until the cold has been treated.

2. The method of claim 1, wherein an effective dosage comprises an amount which is sufficient to provide a zinc ion concentration of between about 0.1 mM and 1 M in the saliva of the human being treated.

3. The method of claim 2, wherein an effective dosage comprises an amount which is sufficient to provide a zinc ion concentration of between about 1 mM and about 300 mM in the saliva of the human being treated.

4. The method of claim 3, wherein an effective dosage comprises an amount which is sufficient to provide a zinc ion concentration of between about 5 mM and about 50 mM in the saliva of the human being treated.

5. The method of claim 1 wherein the zinc compound is zinc ascorbate.

6. The method of claim 1 wherein the zinc compound is zinc acetate.

7. The method of claim 1 wherein the dosage form is a candy.

8. The method of claim 1 wherein the dosage form is a chewing gum.

9. The method of claim 1 wherein the dosage form is a lozenge.

10. The method of claim 1 wherein the dosage form is a troche.

11. The method of claim 1 wherein the dosage form is a tablet.

12. The method of claim 1 wherein the dosage form is a powder.

13. The method of claim 12 wherein the powder is an aerosol.

14. The method of claim 1 wherein the dosage is form is a liquid.

15. The method of claim 14 wherein the liquid is a liquid spray.

16. A method for treating symptoms commonly associated with the common cold, the symptoms including nasal drainage, nasal congestion, headache, fever, myalgia, sneezing, sore throat, scrathy throat, cough or hoarseness to reduce the duration or severity thereof comprising:
  (a) applying an effective dosage of a pharmaceutically acceptable saliva soluble and ionizable zinc compound other than zinc gluconate to the oral mucosa of a human in need of treatment;
  (b) permitting said zinc compound to remain in contact with the oral mucosa for a period of time necessary for the zinc thereof to saturate the oral mucosa; and
  (c) applying additional dosages of such a zinc compound in like fashion until the severity or duration of the symptom has been reduced.

17. The method according to claim 16 wherein an effective dosage comprises an amount which is sufficient to provide a zinc ion concentration of between about 0.1 mM and about 1 M in the salivia of the human being treated.

18. The method according to claim 17 wherein an effective dosage comprises an amount which is sufficient to provide a zinc ion concentration of between about 1 mM and about 300 mM in the salivia of the human being treated.

19. The method of claim 18 wherein an effective dosage comprises an amount which is sufficient to provide a zinc ion concentration of between about 5 mM and about 50 mM in the salivia of the human being treated.

20. The method of claim 16 wherein the zinc compound is zinc ascorbate.

21. The method of claim 16 wherein the zinc compound is zinc acetate.

22. The method of claim 16 wherein the dosage form is a candy.

23. The method of claim 16 wherein the dosage form is a chewing gum.

24. The method of claim 16 wherein the dosage form is a lozenge.

25. The method of claim 16 wherein the dosage form is a troche.

26. The method of claim 16 wherein the dosage form is a tablet.

27. The method of claim 16 wherein the dosage form is a powder.

28. The method of claim 27 wherein the powder is an aerosol.

29. The method of claim 16 wherein the dosage form is a liquid.

30. The method of claim 29 wherein the liquid is a liquid spray.

31. The method of claim 1 wherein the dosage form is a solid dosage form, and said zinc compound is permitted to remain in contact with the oral mucosa for a period of time necessary for the zinc thereof to dissolve.

32. The method of claim 16 wherein the dosage form is a solid dosage form, and said zinc compound is permitted to remain in contact with the oral mucosa for a period of time necessary for the zinc thereof to dissolve.

* * * * *